United States Patent
Wang

(10) Patent No.: US 9,980,843 B2
(45) Date of Patent: May 29, 2018

(54) JOINT SUPPORT ADJUSTABLE DEVICE

(71) Applicant: Meng-Chun Wang, Taichung (TW)

(72) Inventor: Meng-Chun Wang, Taichung (TW)

(*) Notice: Subject to any disclaimer, the term of this patent is extended or adjusted under 35 U.S.C. 154(b) by 404 days.

(21) Appl. No.: 14/962,661

(22) Filed: Dec. 8, 2015

(65) Prior Publication Data

US 2017/0156910 A1 Jun. 8, 2017

(51) Int. Cl.
*A61F 5/01* (2006.01)

(52) U.S. Cl.
CPC .... *A61F 5/0102* (2013.01); *A61F 2005/0167* (2013.01)

(58) Field of Classification Search
CPC ............ A61F 5/0102; A61F 2005/0167; A61F 5/0123; A61F 5/0125; A61F 2005/0139; A61F 5/0111; A61F 5/0585; A61F 5/0127; A61F 5/0195
See application file for complete search history.

(56) References Cited

FOREIGN PATENT DOCUMENTS

TW M336776 U 7/2008
TW M414216 U 10/2011

*Primary Examiner* — Ophelia A Hawthorne
(74) *Attorney, Agent, or Firm* — Muncy, Geissler, Olds & Lowe, P.C.

(57) ABSTRACT

A joint support adjustable device is provided, including a base, two connecting members and a positioning mechanism. The base has a center and two side walls distanced from and corresponding to each other, and at least one said side wall is formed with a plurality of toothed recesses. Each said connecting member is for being connected with a human limb. The positioning mechanism has a fixation member disposed between the two side walls and at least one adjusting mechanism connected with the base, each said adjusting mechanism has a positioning assembly for being operated from outside and movable about the center, at least one of the positioning assembly and the fixation member is magnetic to attract the other so that the positioning assembly has a tendency to move toward the center.

10 Claims, 7 Drawing Sheets

JOINT SUPPORT ADJUSTABLE DEVICE

BACKGROUND OF THE INVENTION

Field of the Invention

The present invention relates to a joint support, and more particularly to a joint support adjustable device.

Description of the Prior Art

Usually, when limbs are wounded, especially when the wounds are near joints (for example, knees), an auxiliary equipment is often used during a healing/recovering process to prevent the wounded parts from being wounded again or worsening due to excessive movement. The auxiliary equipment can restrict the movement of the limbs and protect the limbs. In addition, this type of auxiliary equipment can also be used to correct body postures. This type of joint support adjustable devices are disclosed in TWM336776 and TWM414216.

In TWM336776, a positioning pin is inserted into a positioning hole to adjust and position the joint support adjustable device; however, when the joint support adjustable device is used on the elderly or children whose bodies are weaker, the joint support adjustable device cannot be positioned firmly because the elderly and children are incapable of moving deftly and operating the joint support adjustable device precisely.

In TWM414216, the joint support adjustable device is positioned through a positioning pin being engaged with a toothed recess, wherein an opening of the toothed recess faces a center of a plate body, and an elastic member moves the positioning pin away from the center of the plate body normally so that the joint support adjustable device is positioned. When a user wants to adjust an angle of the joint support adjustable device, s/he can press a pressing button to move or adjust the joint support adjustable device. However, the pressing button radially protrudes out of the plate body; therefore, when the user is moving, the pressing button may be impacted accidentally, and the positioning pin may be disengaged from the toothed recess and unable to position the joint support adjustable device firmly.

The present invention has arisen to mitigate and/or obviate the afore-described disadvantages.

SUMMARY OF THE INVENTION

The major object of the present invention is to provide a joint support adjustable device, wherein an adjusting mechanism can be moved easily to adjust an angle a user wants. In view of unexpected impacts, a positioning orientation is changed, and the joint support adjustable device is positioned through magnetic attraction so that a positioning assembly and a base are positioned preferably and stably, and the safety and reliablilty of using the joint support adjustable device are elevated.

To achieve the above and other objects, a joint support adjustable device is provided, including a base, two connecting members and a positioning mechanism. The base has a center and two side walls distanced from and corresponding to each other, at least one said side wall is formed with a plurality of toothed recesses which are arranged arcuately relative to the center and communicate with each other, and an opening of each said toothed recess is opposite to the center. The two connecting members are connected with the base respectively, at least one of the two connecting members is pivoted to the base, and each said connecting member is for being connected with a human limb. The positioning mechanism has a fixation member disposed between the two side walls and at least one adjusting mechanism connected with the base, each said adjusting mechanism has a positioning assembly for being operated from outside and movable about the center, the positioning assembly is optionally radially movable to be engaged with or disengaged from one said toothed recess, at least one of the positioning assembly and the fixation member is magnetic to attract the other so that the positioning assembly has a tendency to move toward the center.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

Figure 1:
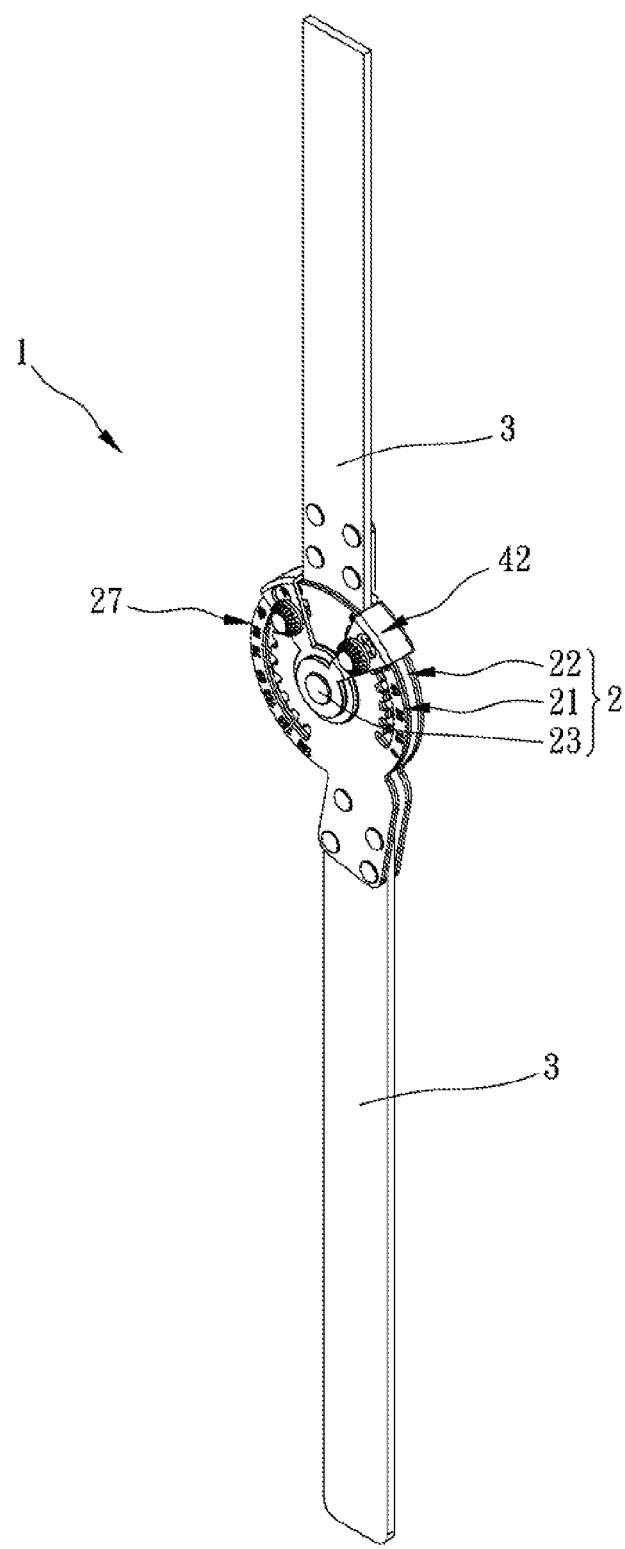
FIG. 1 is a perspective view of a preferred embodiment of the present invention.
Figure 2:
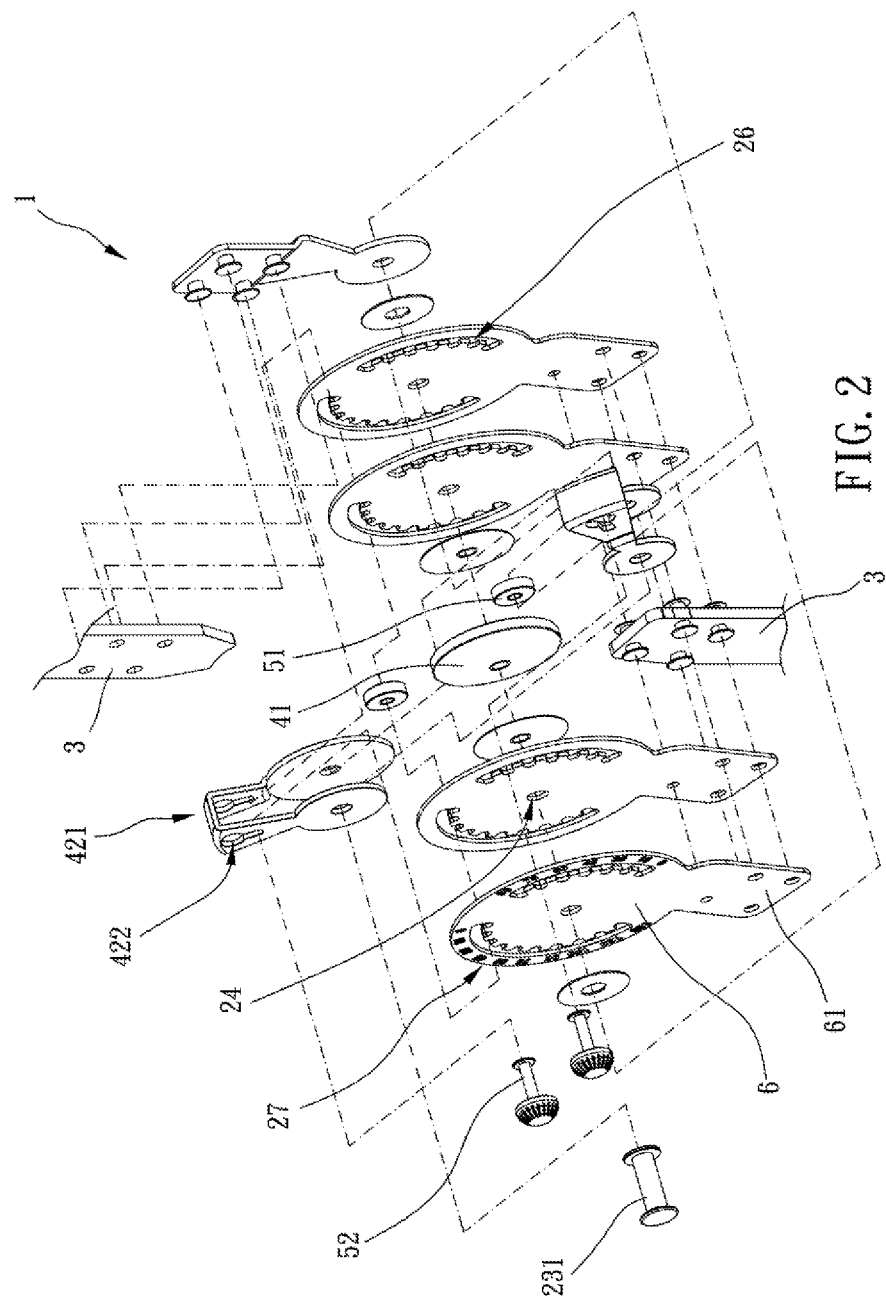
FIG. 2 is a breakdown view of the preferred embodiment of the present invention.
Figure 3:
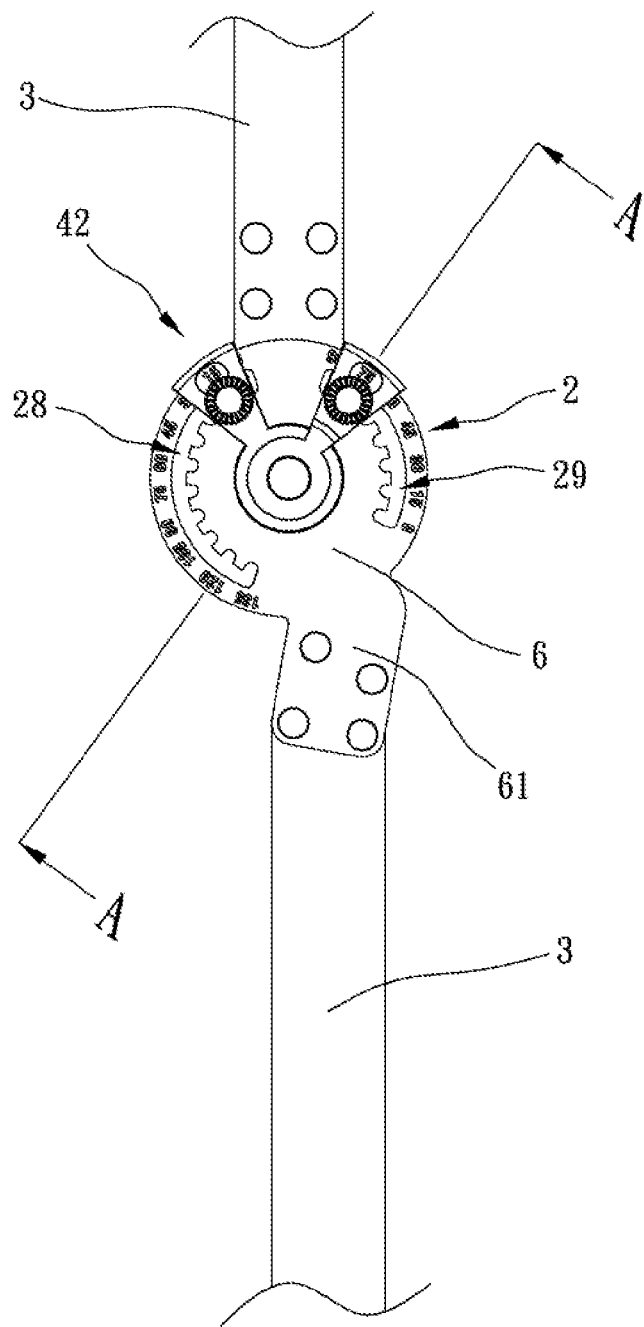
FIG. 3 is a front elevation view of the preferred embodiment of the present invention.
Figure 4:
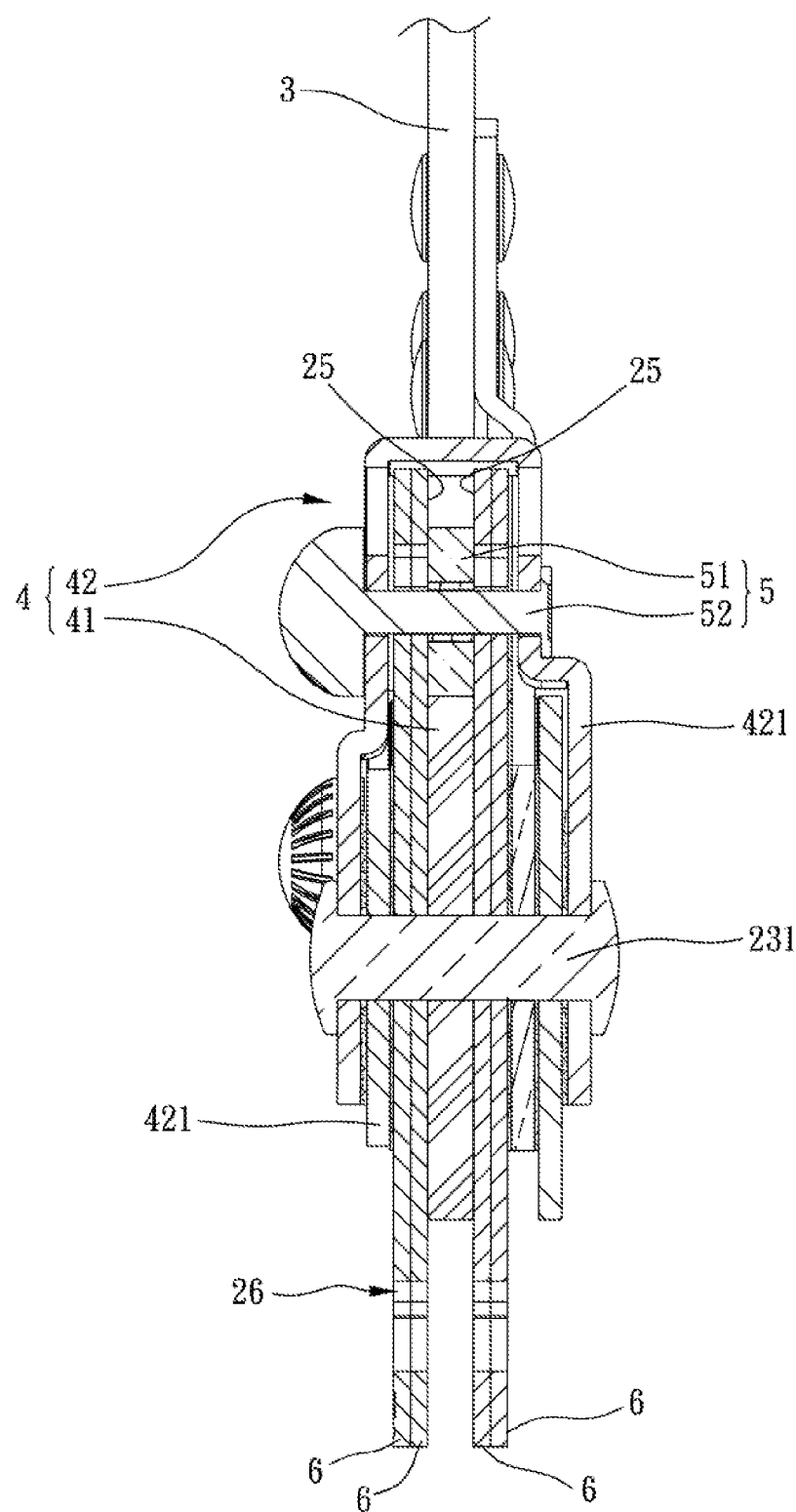
FIG. 4 is a cross-sectional view of the preferred embodiment of the present invention, taken along line A-A in FIG. 3.
Figures 5, 6:
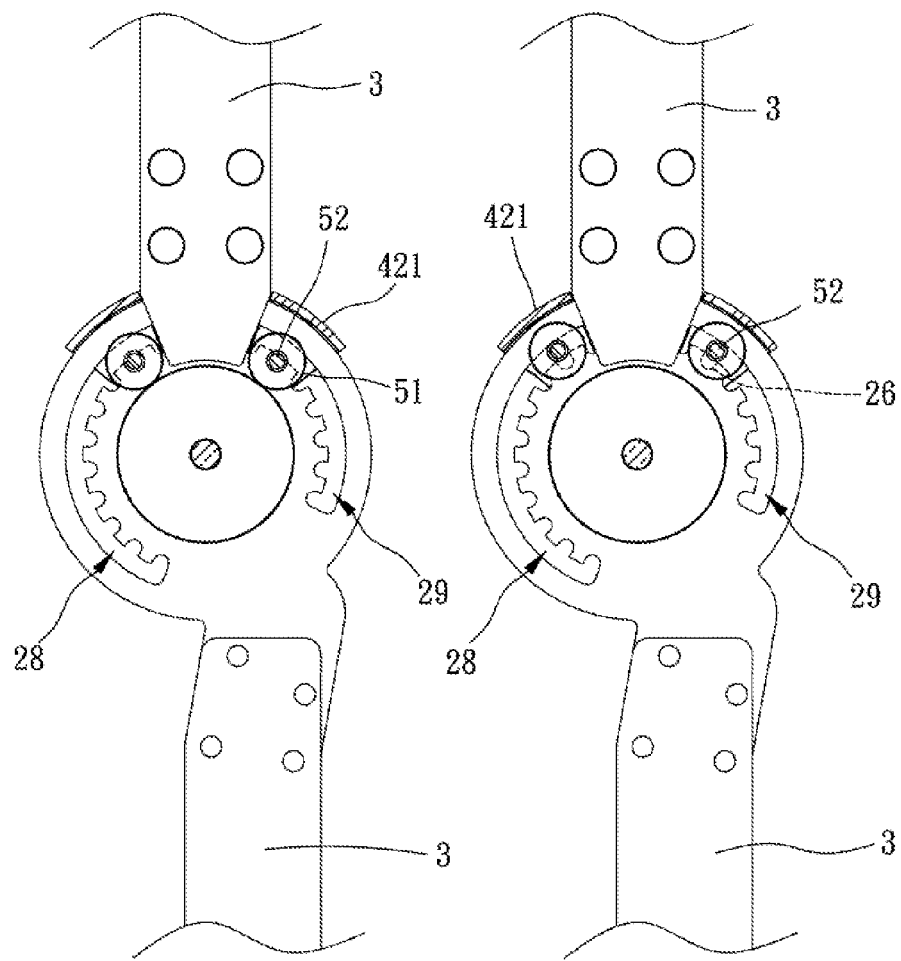
FIGS. 5 to 8 are drawings showing the preferred embodiment of the present invention in use.
Figures 7, 8:
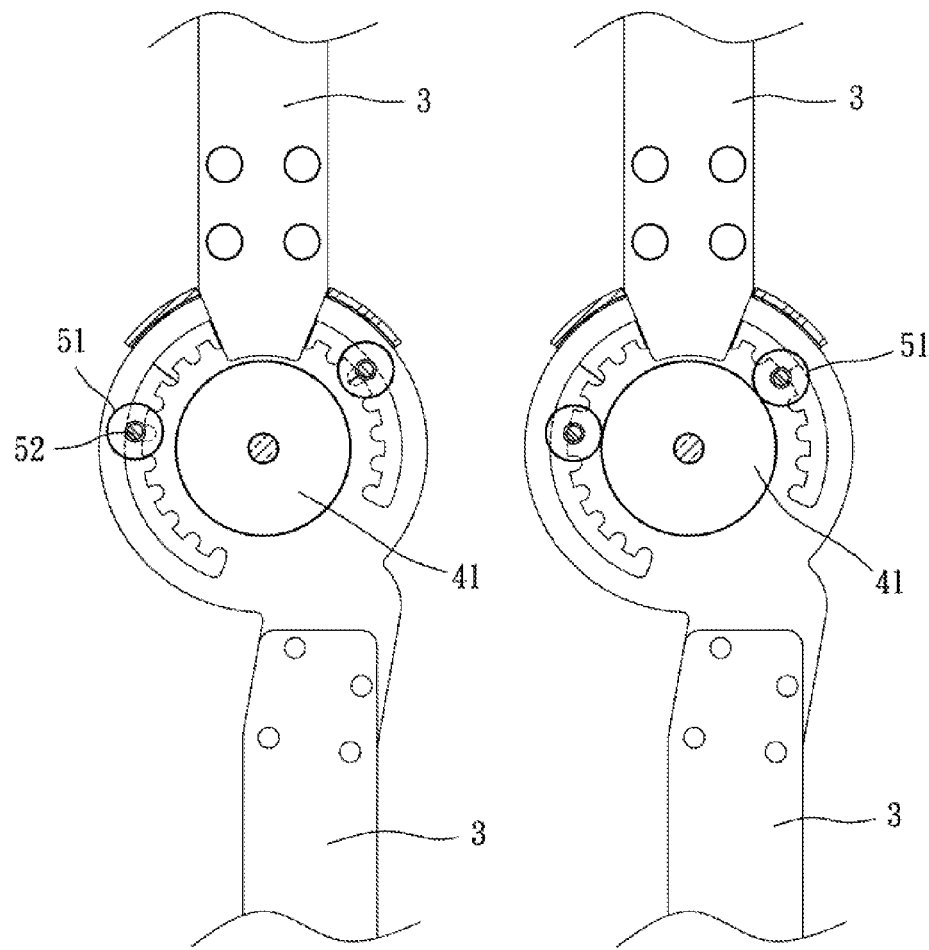

The present invention will be clearer from the following description when viewed together with the accompanying drawings, which show, for purpose of illustrations only, the preferred embodiment in accordance with the present invention.

Please refer to FIGS. 1 to 8 for a preferred embodiment of the present invention. A joint support adjustable device 1 includes a base 2, two connecting members 3 and a positioning mechanism 4.

The base 2 has a center 24 and two side walls 25 distanced from and corresponding to each other, at least one said side wall 25 is formed with a plurality of toothed recesses 26 which are arranged arcuately relative to the center 24 and communicate with each other, and an opening of each said toothed recess 26 is opposite to the center 24. The two connecting members 3 are connected with the base 2 respectively, at least one of the two connecting members 3 is pivoted to the base 2, and each said connecting member 3 is for being connected with a human limb. The positioning mechanism 4 has a fixation member 41 disposed between the two side walls 25 and at least one adjusting mechanism 42 connected with the base 2, each said adjusting mechanism 42 has a positioning assembly 5 for being operated from outside and movable about the center 24, the positioning assembly 5 is optionally radially movable to be engaged with or disengaged from one said toothed recess 26, at least one of the positioning assembly 5 and the fixation member 41 is magnetic to attract the other so that the positioning assembly 5 has a tendency to move toward the center 24.

More specifically, in actual use, impact is exerted mostly from outside toward the center 24; therefore, the positioning assembly 5 is designed to move toward the center 24 to be positioningly engaged with one said toothed recess 26 so as to prevent the positioning assembly 5 from being disengaged due to impact. In addition, through magnetic attraction of the positioning assembly 5 and the fixation member 41, the positioning mechanism 4 is not easily disengaged due to impact.

Preferably, the fixation member 41 is a magnet, and at least part of the positioning assembly 5 is magnetic. Therefore, when the positioning assembly 5 is moved, the positioning assembly 5 receives less resistance, and it is convenient for users (for example, the elderly and children) to operate and position the positioning assembly 5. In addition, the fixation member 41 is a magnet which is positioningly fixed, so each said positioning assembly 5 can be located on any position of the base 2 and be magnetically attracted by the fixation member 41 to move toward the center 24. In other words, the positioning mechanism 4 is automatically repositionable.

More specifically, each said positioning assembly 5 has a movable member 51 disposed between the two side walls 25 and a pin 52 disposed through the movable member 51, and the pin 52 is optionally radially movable to be engaged with or disengaged from one said toothed recess 26. It is understandable that at least one of the movable member 51 and the fixation member 41 is magnetic to attract the other so that the movable member 51 has the tendency to move toward the center 24.

In this embodiment, the movable member 51 may be magnetically attractable. It is understandable that, in other embodiments, the pin 52 may be magnetically attractable to be attracted by the fixation member 41 as long as the positioning assembly 5 and the fixation member 41 are magnetically attractable to each other. Specifically, the fixation member 41 and each said movable member 51 are disc-like, and when the pin 52 is engaged with one said toothed recess 26, each said movable member 51 contacts a circumferential face of the fixation member 41. More specifically, as viewed in an axial direction passing the center 24, the fixation member 41 does not protrude out of the toothed recesses 26, so the pin 52 can be engaged with one said toothed recess 26 firmly.

Furthermore, it is to be noted that the base 2 includes a first assembly 21, a second assembly 22 arranged spacingly and correspondingly to the first assembly 21 and a connecting portion 23 connected with the first and second assemblies 21, 22, and each of the first and second assemblies 21, 22 has one said side wall 25, wherein the first and second assemblies 21, 22 respectively include at least one plate 6, and at least one said plate 6 is formed with the toothed recesses 26. In this embodiment, the connecting portion 23 is a pivot axle 231, the pivot axle 231, the fixation member 41 and the first and second assemblies 21, 22 are coaxially arranged, and the first and second assemblies 21, 22 respectively include two said plates 6; therefore, a structural strength of the base 2 is improved. In addition, one of the two connecting members 3 is fixedly disposed between the two side walls 25, the other of the two connecting members 3 is pivoted to the base 2. Specifically, each said plate 6 is formed with the toothed recesses 26 and radially extends to form a wing portion 61. Each said wing portion 61 and one of the two connecting members 3 are fixedly engaged with each other, the other of the two connecting members 3 is pivoted to the pivot axle 231, and when viewed in an extension direction of the pivot axle 231, a contour of each said plate 6 is substantially 9-shaped.

Furthermore, in this embodiment, each said adjusting mechanism 42 is further provided with a movable base 421 which is pivoted to the pivot axle 231, each said movable base 421 is saddled on the first and second assemblies 21, 22, and the two positioning assemblies 5 are movably disposed on the two movable bases 421. When in use, the positioning assembly 5 is moved to be disengaged from one said toothed recess 26, then the movable base 421 and the positioning assembly 5 are rotated to move about the center 24, when the movable base 421 and the positioning assembly 5 are rotated to a position the user wants, s/he only needs to loosen his/her grip, then the positioning assembly 5 can move relative to the movable base 421 to be engaged with one said toothed recess 26, and the positioning mechanism 4 is positioned. Preferably, the base 2 is further formed with a plurality of degree scales 27, and the degree scales 27 respectively correspond to the toothed recesses 26. When the movable base 421 is rotated, the user can see the degree clearly and adjust the movable base 421 to a precise swing range s/he wants. More preferably, each said movable base 421 is further formed with an identification hole 422, the identification hole 422 corresponds to one said degree scale 27, and the user can see the degree scale 27 through the identification hole 422. In addition, each said identification hole 422 may be additionally provided with a magnifying glass for the users who are poor-sighted.

More specifically, the base 2 is formed with a first slide groove 28 and a second slide groove 29 which are arranged arcuately relative to the center 24, and the first and second slide grooves 28, 29 are incommunicable with each other. It is understandable that the positioning mechanism 4 has two said adjusting mechanisms 42, the first and second slide grooves 28, 29 are respectively formed with the toothed recesses 26, and the two positioning assemblies 5 are slidably disposed in the first and second slide grooves 28, 29. A swinging range of the two connecting members 3 swinging relative to each other can be controlled through adjusting a relative position of the two adjusting mechanisms 42. More specifically, the first slide groove 28 is greater than the second slide groove 29 in arc length, the first slide groove 28 ranges between 0 and 135 degrees, and the second slide groove 29 ranges between 0 and 90 degrees, wherein a gap between two said degree scales 27 neighboring to each other is 15 degrees. In other embodiments, the arc lengths of the first and second slide grooves 28, 29 and the gap between two said degree scales 27 neighboring to each other may be changed in accordance with different requirements.

Figure 9:
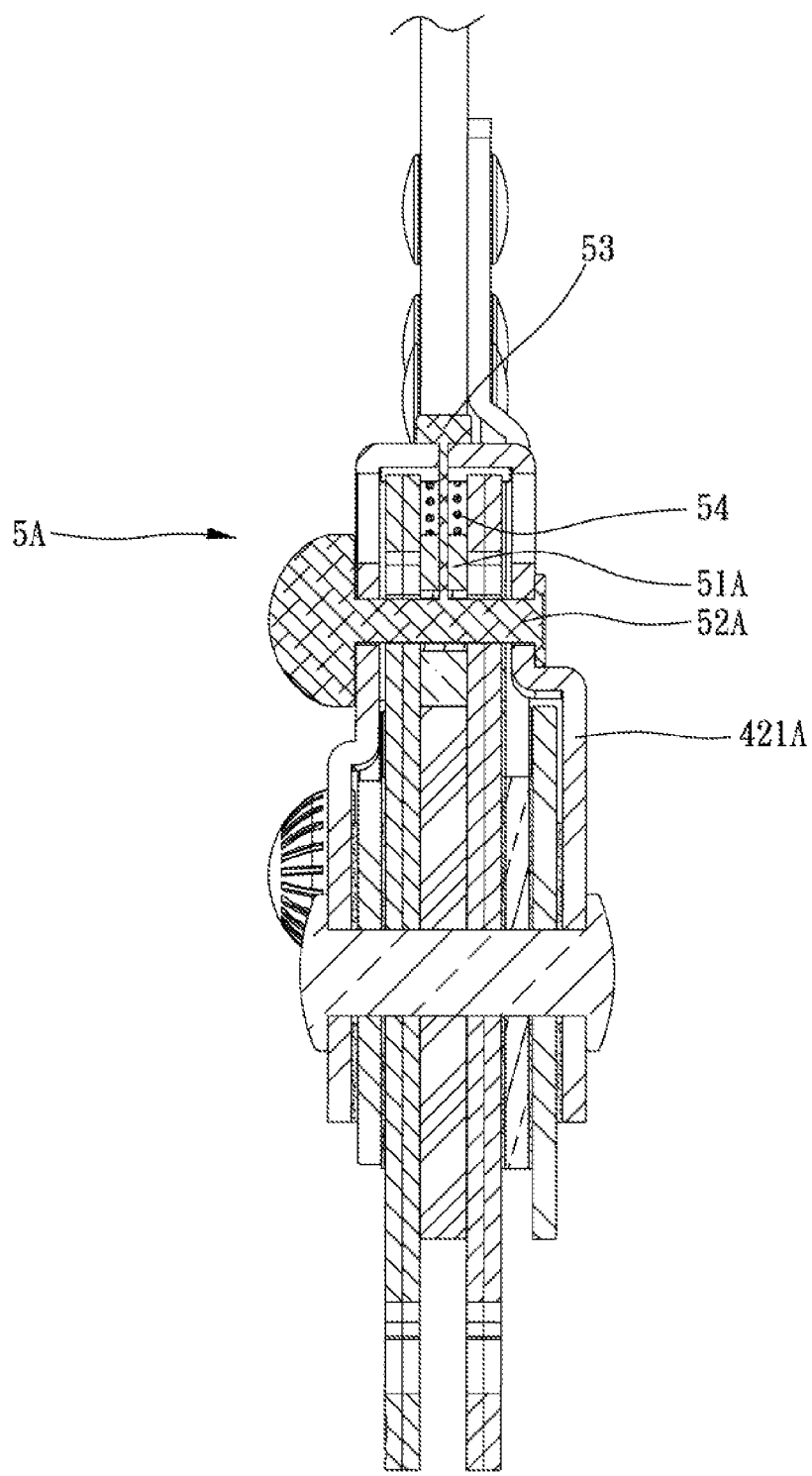
FIG. 9 is a cross-sectional view of another preferred embodiment of the present invention.

Please refer to FIG. 9 for another preferred embodiment. A positioning assembly 5A is further formed with an adjusting member 53 transverse to a pin 52A and an elastic member 54. An end of the adjusting member 53 is disposed through the movable base 421A and the movable member 51A to be engaged with the pin 52A, the adjusting member 53 is for being operated from outside to drive the pin 52A and the movable member 51A to move radially to be engaged with or disengaged from one said toothed recess, and two ends of the elastic member 54 respectively abut against the movable base 421A and the movable member 51A. Therefore, the user can disengage the pin 52A and the movable member 51A from one said toothed recess through pulling the adjusting member 53. In addition, when the user loosens grip of the adjusting member 53, the elastic member 54 makes the pin 52A and the movable member 51A move toward the center, wherein the adjusting member 53 is screwed with the pin 52A, and in other embodiments, the adjusting member 53 and the pin 52A may be engaged with each other in other ways.

Given the above, considering the users in different ages and body states, the positioning mechanism is improved so that the user can move and position the positioning mechanism through moving the pin radially to be engaged with the toothed recess.

In addition, the fixation member and the movable member magnetically attract each other, so the positioning assembly has the tendency to move toward the center on any position and is automatically repositionable.

Furthermore, connection through magnetic attraction makes the stability of positioning largely elevated, and the joint support adjustable device is not easily disengaged due to impact.

While we have shown and described various embodiments in accordance with the present invention, it should be clear to those skilled in the art that further embodiments may be made without departing from the scope of the present invention.

What is claimed is:

1. A joint support adjustable device, including:
a base, having a center and two side walls distanced from and corresponding to each other, at least one said side wall being formed with a plurality of toothed recesses which are arranged arcuately relative to the center and communicate with each other, an opening of each said toothed recess being opposite to the center;
two connecting members, connected with the base respectively, at least one of the two connecting members pivoted to the base, each said connecting member for being connected with a human limb;
a positioning mechanism, having a fixation member disposed between the two side walls and at least one adjusting mechanism connected with the base, each said adjusting mechanism having a positioning assembly for being operated from outside and movable about the center, the positioning assembly being optionally radially movable to be engaged with or disengaged from one said toothed recess, at least one of the positioning assembly and the fixation member being magnetic to attract the other so that the positioning assembly has a tendency to move toward the center.

2. The joint support adjustable device of claim 1, wherein each said positioning assembly has a movable member located between the two side walls and a pin disposed through the movable member, the pin is optionably radially movable to be engaged with or disengaged from one said toothed recess, at least one of the movable member and the fixation member is magnetic to attract the other so that the movable member has the tendency to move toward the center.

3. The joint support adjustable device of claim 2, wherein the fixation member is a magnet, and the movable member is magnetically attractable.

4. The joint support adjustable device of claim 2, wherein each said adjusting mechanism is further provided with a movable base which is pivoted to the connecting portion, each said movable base is saddled on the base, the positioning assembly is movably disposed on the movable base, the positioning assembly is further provided with an adjusting member transverse to the pin and an elastic member, an end of the adjusting member is disposed through the movable base and the movable member to be engaged with the pin, the adjusting member is for being operated from outside to drive the pin and the movable member to move radially and further to be engaged with or disengaged from one said toothed recess, and two ends of the elastic member respectively abut against the movable base and the movable member.

5. The joint support adjustable device of claim 1, wherein the base includes a first assembly, a second assembly which is arranged spacingly and correspondingly to the first assembly and a connecting portion which is connected with the first and second assemblies, each of the first and second assemblies has one said side wall, each of the first and second assemblies includes at least one plate, and at least one said plate is formed with the toothed recesses.

6. The joint support adjustable device of claim 1, wherein the fixation member is a magnet, and at least part of the positioning assembly is magnetically attractable.

7. The joint support adjustable device of claim 1, wherein one of the two connecting members is fixedly disposed between the two side walls, and the other of the two connecting members is pivoted to the base.

8. The joint support adjustable device of claim 1, wherein the base is further formed with a plurality of degree scales, and the degree scales correspond to the toothed recesses respectively.

9. The joint support adjustable device of claim 1, wherein the base is formed with a first slide groove and a second slide groove which are arranged arcuately relative to the center, the first and second slide grooves are incommunicable with each other, the positioning mechanism has two said adjusting mechanisms, the first and second slide grooves are respectively formed with the toothed recesses, and the two positioning assemblies are slidably disposed in the first and second slide grooves.

10. The joint support adjustable device of claim 9, wherein when viewed in an axial direction passing the center, the fixation member non-protrudes out of the toothed recesses, the base includes a first assembly, a second assembly which is arranged spacingly and correspondingly to the first assembly and a connecting portion which is connected with the first and second assemblies, each of the first and second assemblies has one said side wall, the connecting portion is a pivot axle, the pivot axle, the fixation member and the first and second assemblies are coaxially arranged, the first and second assemblies respectively include two plates, each said plate is formed with a plurality of the toothed recesses and extends radially to form a wing portion, each said wing portion and one of the two connecting members are fixedly engaged with each other, the other of the two connecting members is pivoted to the pivot axle, when viewed in an extension direction along the pivot axle, a contour of each said plate is substantially 9-shaped; each said adjusting mechanism is further provided with a movable base pivoted to the pivot axle, each said movable base is saddled on the first and second assemblies, the two positioning assemblies are movably disposed on the two movable bases; each said positioning assembly has a movable member located between the two side walls and a pin disposed through the movable member, the pin is optionably radially movable to be engaged with or disengaged from one said toothed recess, at least one of the movable member and the fixation member is magnetic to attract the other so that the movable member has the tendency to move toward the center; wherein the fixation member is a magnet, the movable member is magnetically attractable; the fixation member and each said movable member are disc-like, when the pin is engaged with one said toothed recess, each said movable member contacts a circumferential face of the fixation member; the base is further formed with a plurality of degree scales, the degree scales correspond to the toothed recesses respectively, each said movable base is further formed with an identification hole, the identification hole corresponds to one said degree scale, a gap between two neighboring degree scales is 15 degrees, wherein the first slide groove is greater than the second slide groove in arc length, the first slide groove ranges between 0 and 135 degrees, and the second slide groove ranges between 0 and 90 degrees.

* * * * *